(12) United States Patent
Gao

(10) Patent No.: US 9,624,742 B2
(45) Date of Patent: Apr. 18, 2017

(54) AUTOMATIC ROCK DEBRIS CATCHING AND WASHING APPARATUS

(71) Applicant: Shijiazhuang Shengshitiancheng Info Technology Co. Ltd., Shijiazhuang (CN)

(72) Inventor: Xing Gao, Shijiazhuang (CN)

(73) Assignee: SHIJIAZHUNG SHENGSHITIANCHENG INFO TECHNOLOGY CO. LTD., Shijiazhuang (CN)

( * ) Notice: Subject to any disclaimer, the term of this patent is extended or adjusted under 35 U.S.C. 154(b) by 34 days.

(21) Appl. No.: 14/851,363

(22) Filed: Sep. 11, 2015

(65) Prior Publication Data

US 2017/0009540 A1    Jan. 12, 2017

(30) Foreign Application Priority Data

Jul. 7, 2015   (CN) .......................... 2015 1 0393723

(51) Int. Cl.
E21B 21/06 (2006.01)
B08B 3/02 (2006.01)
B08B 9/093 (2006.01)

(52) U.S. Cl.
CPC .............. *E21B 21/066* (2013.01); *B08B 3/02* (2013.01); *B08B 9/093* (2013.01)

(58) Field of Classification Search
None
See application file for complete search history.

(56) References Cited

U.S. PATENT DOCUMENTS 9,410,387 B1 *   8/2016   Gao ....................... E21B 21/066

FOREIGN PATENT DOCUMENTS

CN    203241269 U   * 10/2013   ............... G01N 1/10

OTHER PUBLICATIONS

English machine translation of CN203241269U.*

* cited by examiner

*Primary Examiner* — Michael Barr
*Assistant Examiner* — Jason Riggleman
(74) *Attorney, Agent, or Firm* — Carter, DeLuca, Farrell & Schmidt, LLP

(57) ABSTRACT

An automatic rock debris catching and washing apparatus comprises an acquisition device, a filtration device and a collection device. The filtration device comprises a water collection tank, above which a driving motor is connected with a pendulum bar having an end connected with a filtering scoop for receiving rock debris from the screening cylinder. The water collection tank is provided with a helical conveying rod having one end located at the bottom of the water collection tank and the other end located outside the water collection tank. A delivery pump is provided at the bottom of the water collection tank. The apparatus has a full-automatic collection operation. During use, it is not necessary to real-time monitor working condition of the catching and washing apparatus by manpower. Collecting regularly rock debris collected into the sand storing cylinders is enough. It is adaptable to the harsh environment, accurate in operation and analysis.

10 Claims, 4 Drawing Sheets

AUTOMATIC ROCK DEBRIS CATCHING AND WASHING APPARATUS

TECHNICAL FIELD

The present invention relates to the field of petroleum drilling geological logging equipment, and particularly to an automatic rock debris catching and washing apparatus.

BACKGROUND ART

In the process of petroleum drilling, drilling rock debris underground is carried to the ground by high-speed mud flowing in a drilling tool, and then the debris is filtered out by means of a mud vibration shaker. The geological features at the drilling position are derived by collecting and analyzing the rock debris. For a long time, the rock debris is collected manually at the construction site, and then the rock debris, surfaces of which the drilling mud is adhered to, are cleaned with water, and taken to a geologic room to make geological analysis.

A drilling operation requires dozens of days or several months of drilling, the geological logging requires catching the rock debris samples every 1 to 2 meters, with the shortest sampling interval of 1 to 2 minutes. Every time, the weight of the rock debris is about 500 grams. No matter it is daytime or nighttime or it is rainy or windy, or it is freezing winter or sultry summer, the sampling must be carried out strictly according to the construction schedule. Therefore, it is a heavy work in the case of manual operation, and the working environment is very harsh. Also, it is prone to cause error in the process of manually acquiring rocks, resulting in confusion to the geological analysis of rock debris, directly affecting geological interpretation and effects of petroleum exploration and development.

DISCLOSURE OF THE INVENTION

An object of the present invention is to provide an automatic rock debris catching and washing apparatus, so as to solve the problems in the prior art, which is of harsh and unsafe working environment and being prone to cause error in the manual collection approach.

The automatic rock debris catching and washing apparatus provided by the present invention comprises an acquisition device, a filtration device and a collection device.

The acquisition device comprises a delivery pipe, one end of which is corresponding to an acquisition port and the other end of which is a delivery port. The acquisition port is provided on an acquisition pipe, with the acquisition port is a strip-shaped acquisition port, the delivery pipe is sleeved over the acquisition pipe, the acquisition pipe and the delivery pipe can make telescopic movement relative to each other. The delivery port is connected with a filtering head, which comprises a bearing provided on the delivery port, an impeller is provided in the bearing, the impeller is connected to a driving device, and one end of the bearing away from the delivery pipe is connected with a screening cylinder, one end of which is fixedly connected with the bearing and in a side wall of which filtering holes are provided.

The filtration device comprises a water collection tank, above which a driving motor is provided. The driving motor is connected with a pendulum bar, one end of which is connected with a filtering scoop for receiving rock debris flowing out of the screening cylinder. The water collection tank is provided therein with a helical conveying rod, one end of which is located at a bottom of the water collection tank, and the other end of which is located outside of the water collection tank. A delivery pump for delivering mortar towards a helical conveying rod is provided at the bottom of the water collection tank.

The collection device comprises a collection chamber, on which a funnel is provided, with the funnel used for receiving rock debris poured by the filtering scoop. A cleaning sprayer is connected at an outlet of the funnel, and a fresh water pipe is connected with the cleaning sprayer. In the collection chamber is a rotating disk provided, with the rotating disk having a bottom connected with a stepper motor and a top provided with a plurality of sand storing cylinders arranged in an annular shape, and the cleaning sprayer is arranged opposite to inlets of the sand storing cylinders.

Furthermore, the automatic rock debris catching and washing apparatus further comprises a controlling device, which comprises an explosion-proof box having a controller, which is connected to the driving device, the driving motor and the stepper motor.

Furthermore, a rain pipe is provided at an inlet of the funnel, with the rain pipe having one end being closed, and the other end placed in the water collection tank and connected with a first water pump, which is connected to the controller.

Furthermore, a fresh water tank is provided in the collection tank, the fresh water tank is provided with a fresh water inlet and a fresh water outlet, which is connected with the fresh water pipe, and at the fresh water outlet is a second pump provided, with the second pump connected to the controller.

Furthermore, a vehicle cleaning tank is provided in the water collection tank, the vehicle cleaning tank is provided with a water inlet and a water outlet, which is communicated with the water collection tank and connected to a third pump is connected to the controller.

Furthermore, a drainage port is provided on the water collection tank and connected with a drainage pump, which is connected to the controller.

Furthermore, a backup delivery pump is provided at a bottom of the water collection tank.

Furthermore, the bottom of the water collection tank, in a shape of funnel, is provided with an opening, and a solenoid valve is provided on the opening.

Furthermore, diameter of the screening cylinder is gradually reduced from middle of the screening cylinder towards two ends thereof.

Furthermore, a protective cover for covering and connecting the screening cylinder, the filtering scoop and the funnel is provided on a top of the water collection tank, and a bottom of the protective cover is connected to the water collection tank.

When using the automatic rock debris catching and washing apparatus provided by the present invention, mixture of water and rock debris in the delivery pipe enters the screening cylinder, in vortex state, under action of the impeller, and a first filtration is performed in the screening cylinder. After part of the water is filtered out, mixture of the rock debris and a small amount of water is discharged into the filtering scoop, in which a second filtration is performed, with the water filtered out directly entering the water collection tank. The rock debris after the filtration, in the filtering scoop, enters the funnel, under action of the pendulum bar, and then enters the sand storing cylinders to be collected.

The operation is a full-automatic collection approach, which is performed fully automatically. During use, it is not necessary to real-time monitor the working condition of the catching and washing apparatus by manpower, and collecting regularly the rock debris, which is collected into the sand storing cylinders, is enough. It is highly adaptable to the harsh environment due to the mechanized processing, with higher accuracy and more accurate analysis on geological conditions.

BRIEF DESCRIPTION OF DRAWINGS

In order to more clearly illustrate technical solutions of embodiments of the present invention or the prior art, drawings for description of the embodiments or the prior art will be described briefly below. It is obvious that the drawings in the following description only show some embodiments of the present invention, based on which other drawings can be obtained for those ordinary skilled in the art without creative efforts.

LIST OF REFERENCE NUMBERS

Figure 1:
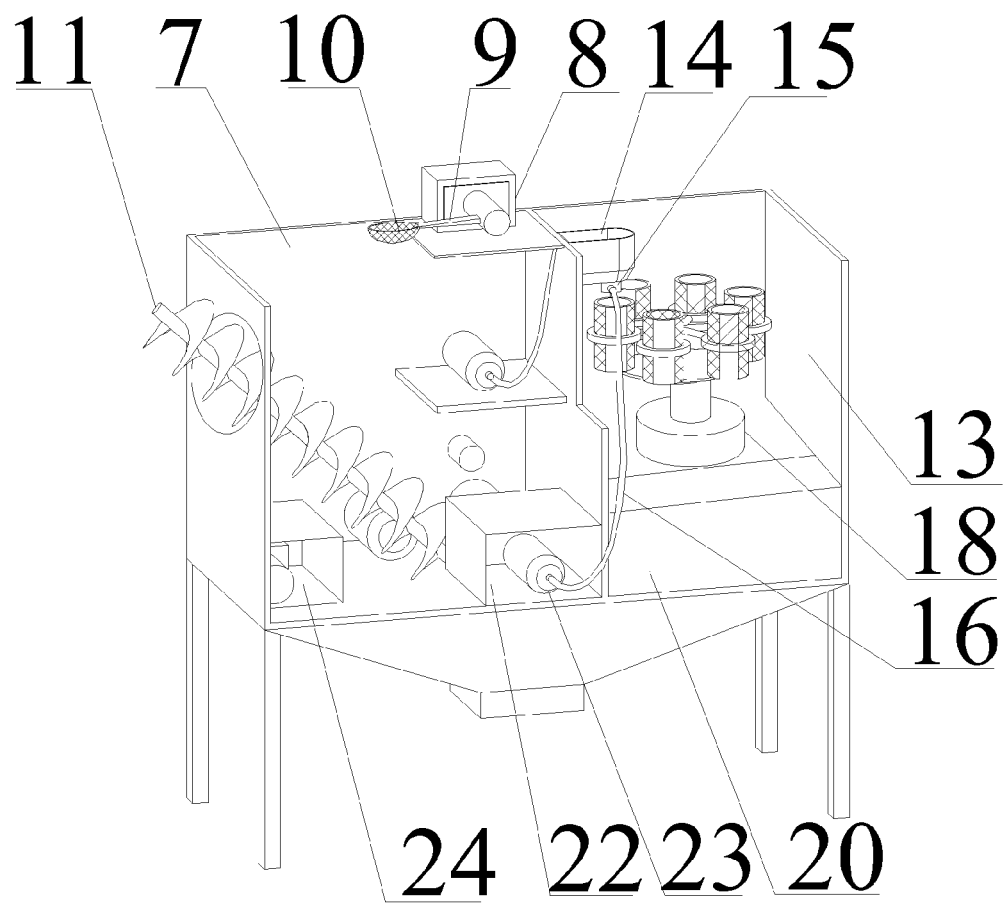
FIG. 1 is a structural schematic diagram of an automatic rock debris catching and washing apparatus provided by an embodiment of the present invention.

| 1-delivery pipe; | 2-acquisition pipe; |
|---|---|
| 3-acquisition port; | 4-bearing; |
| 5-impeller; | 6-screening cylinder; |
| 7-water collection tank; | 8-driving motor; |
| 9-pendulum bar; | 10-filtering scoop; |
| 11-helical conveying rod; | 12-delivery pump; |
| 13-collection chamber; | 14-funnel; |
| 15-cleaning sprayer; | 16-fresh water pipe; |
| 17-rotating disk; | 18-stepper motor; |
| 19-sand storing cylinder; | 20-explosion-proof box; |
| 21-first water pump; | 22-fresh water tank; |
| 23-second water pump; | 24-vehicle cleaning tank; |
| 25-third water pump; | 26-drainage pump; |
| 27-backup delivery pump; | 28-solenoid valve; |
| 29-protective cover. | |

DETAILED DESCRIPTION OF EMBODIMENTS

Below, the technical solutions of the present invention will be described clearly and completely in conjunction with figures. Obviously, the described embodiments are part of embodiments of the present invention, but not all embodiments. Based on the embodiments of the present invention, all other embodiments obtained by those ordinary skilled in the art without creative efforts are within the scope of protection of the present invention.

In the description of the present invention, it should be noted that the orientation or positional relationship indicated by the terms "center", "upper", "lower", "left", "right", "vertical", "horizontal", "inner", "outer", etc. are based on the orientation or position relationship shown in the drawings, only for facilitating and simplifying the description of the present invention, but not for indicating or implying that the devices or elements referred to must have the particular orientation or be configured and operated with the particular orientation, and therefore it should not be construed as limitation to the present invention. In addition, the terms "first", "second", "third", etc. are used only for descriptive purpose and not construed to indicate or imply these relative relationships are of importance.

In the description of the present invention, it should be noted that unless otherwise clearly defined and limited, the terms "mount", "connect", "connecting" are to be understood in broad sense, for example, it may be either fixed connection or detachable connection, or may be integrally connected. It may be either mechanical connection or electrical connection; and it may be either directly connected or connected indirectly through an intermediate member, or it may be the internal communication between two elements. For those ordinary skilled in the art, it can be understood that the above terms have specific meanings in the present invention according to specific circumstances.

Embodiment 1

Figure 2:
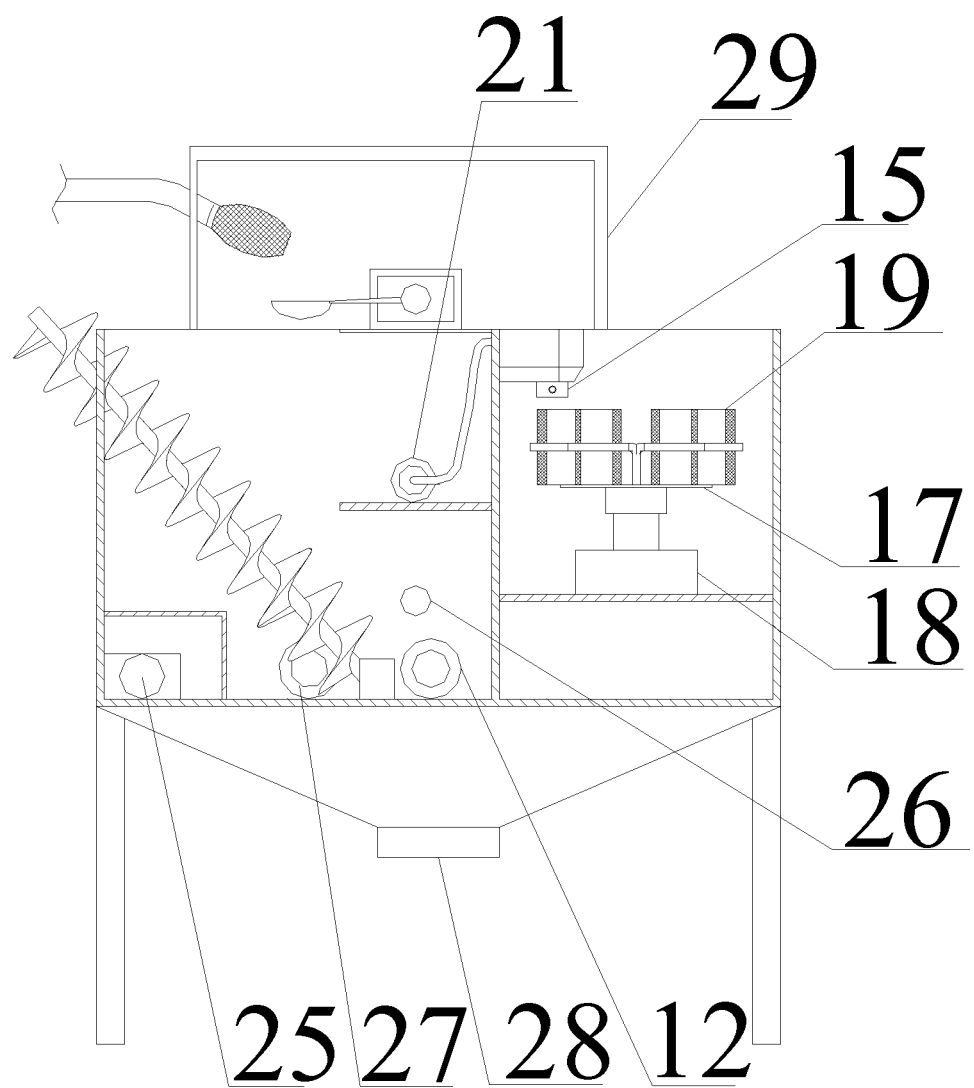
FIG. 2 is a sectional view of the automatic rock debris catching and washing apparatus provided by the embodiment of the present invention.
Figure 3:
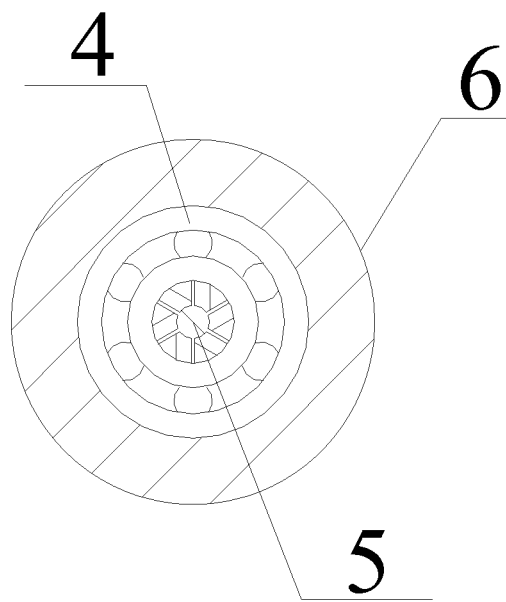
FIG. 3 is a sectional view of a screening cylinder of the automatic rock debris catching and washing apparatus provided by the embodiment of the present invention.
Figure 4:
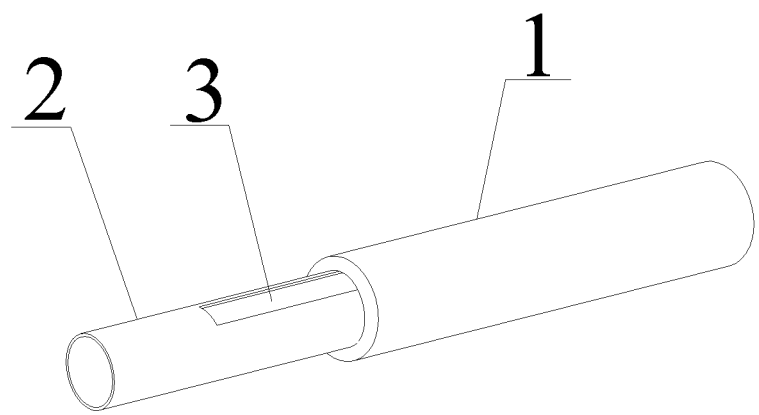
FIG. 4 is a structural schematic diagram of an acquisition port of the automatic rock debris catching and washing apparatus provided by the embodiment of the present invention.
Figure 5:
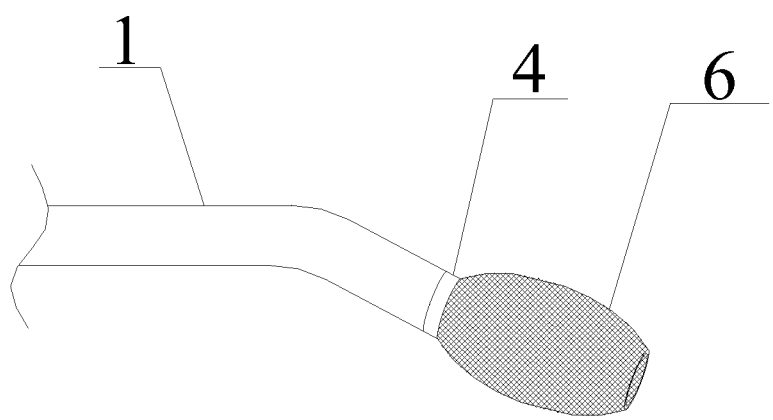
FIG. 5 is a structural schematic diagram of a delivery port of the automatic rock debris catching and washing apparatus provided by the embodiment of the present invention.

FIG. 1 is a structural schematic diagram of an automatic rock debris catching and washing apparatus provided by an embodiment of the present invention; FIG. 2 is a sectional view of the automatic rock debris catching and washing apparatus provided by the embodiment of the present invention; FIG. 3 is a sectional view of a screening cylinder 6 of the automatic rock debris catching and washing apparatus provided by the embodiment of the present invention;

FIG. 4 is a structural schematic diagram of an acquisition port 3 of the automatic rock debris catching and washing apparatus provided by the embodiment of the present invention; and FIG. 5 is a structural schematic diagram of a delivery port of the automatic rock debris catching and washing apparatus provided by the embodiment of the present invention. As shown in FIGS. 1-5, the automatic rock debris catching and washing apparatus provided by this embodiment comprises an acquisition device, a filtration device and a collection device.

The acquisition device comprises a delivery pipe 1, one end of which is corresponding to an acquisition port 3 and the other end of which is a delivery port. The acquisition port 3 is provided in an acquisition pipe 2, with the acquisition port 3 in the strip shape. The delivery pipe 1 is sleeved over the acquisition pipe 2, and the acquisition pipe 2 and the delivery pipe 1 can make telescopic movement relative to each other. The delivery port is connected with a filtering head, which comprises a bearing 4 provided on the delivery port. An impeller 5 is provided in the bearing 4, and the impeller 5 is connected to a driving device. One end of the bearing 4 away from the delivery pipe 1 is connected with a screening cylinder 6, which has one end fixedly connected with the bearing 4 and is provided with filtering holes in the side wall thereof.

The filtration device comprises a water collection tank 7, above which a driving motor 8 is provided. The driving motor 8 is connected with a pendulum bar 9, one end of which is connected with a filtering scoop 10 for receiving rock debris flowing out of the screening cylinder 6. In the water collection tank 7 is a helical conveying rod 11 provided, one end of which is located at the bottom of the water collection tank 7, and the other end of which is located outside of the water collection tank 7. A delivery pump 12 for delivering mortar towards the helical conveying rod 11 is provided at the bottom of the water collection tank 7.

The collection device comprises a collection chamber 13, on which a funnel 14 is provided for receiving the rock debris poured by the filtering scoop 10. A cleaning sprayer 15 is connected at the outlet of the funnel 14, and a fresh water pipe 16 is connected with the cleaning sprayer 15. In the collection chamber 13 is a rotating disk 17 provided, with the rotating disk having the bottom connected with a stepper motor 18 and the top provided with a plurality of sand storing cylinders 19 which are arranged in an annular shape. The cleaning sprayer 15 is arranged opposite to the inlets of the sand storing cylinders 19.

When using the automatic rock debris catching and washing apparatus provided by the present invention, mixture of water and rock debris in the delivery pipe 1 enters the screening cylinder 6, in vortex state, under action of the impeller 5, and a first filtration is performed in the screening cylinder 6. After part of the water is filtered out, mixture of the rock debris and a small amount of water is discharged into the filtering scoop 10, in which a second filtration is performed, with the water filter out directly entering the water collection tank 7. The rock debris after the filtration, in the filtering scoop 10, enters the funnel 14, under the action of the pendulum bar, and then enters the sand storing cylinders 19 to be collected.

The operation is a full-automatic collection approach, which is performed fully automatically. During use, it is not necessary to real-time monitor the working condition of the catching and washing apparatus by manpower, and collecting regularly the rock debris which is collected into the sand storing cylinders 19 is enough. It is highly adaptable to the harsh environment due to the mechanized processing, with high accuracy and more accurate analysis on the geological conditions.

Embodiment 2

FIG. 1 is a structural schematic diagram of an automatic rock debris catching and washing apparatus provided by an embodiment of the present invention; FIG. 2 is a sectional view of the automatic rock debris catching and washing apparatus provided by the embodiment of the present invention; FIG. 3 is a sectional view of a screening cylinder 6 of the automatic rock debris catching and washing apparatus provided by the embodiment of the present invention; FIG. 4 is a structural schematic diagram of an acquisition port 3 of the automatic rock debris catching and washing apparatus provided by the embodiment of the present invention; and FIG. 5 is a structural schematic diagram of a delivery port of the automatic rock debris catching and washing apparatus provided by the embodiment of the present invention. As shown in FIGS. 1-5, the automatic rock debris catching and washing apparatus provided by this embodiment comprises an acquisition device, a filtration device and a collection device.

The acquisition device comprises a delivery pipe 1, one end of which is corresponding to an acquisition port 3 and the other end of which is a delivery port. The acquisition port 3 is provided on an acquisition pipe 2, with the acquisition port 3 in the strip shape. The delivery pipe 1 is sleeved over the acquisition pipe 2, and the acquisition pipe 2 and the delivery pipe 1 can make telescopic movement relative to each other. The delivery port is connected with a filtering head, which comprises a bearing 4 provided on the delivery port. An impeller 5 is provided in the bearing 4, and the impeller 5 is connected to a driving device. One end of the bearing 4 away from the delivery pipe 1 is connected with a screening cylinder 6, which has one end fixedly connected with the bearing 4 and is provided with filtering holes on the side wall thereof.

The filtration device comprises a water collection tank 7, above which a driving motor 8 is provided. The driving motor 8 is connected with a pendulum bar 9, one end of which is connected with a filtering scoop 10 for receiving rock debris flowing out of the screening cylinder 6. In the water collection tank 7 is a helical conveying rod 11 provided, one end of which is located at the bottom of the water collection tank 7, and the other end of which is located outside of the water collection tank 7. A delivery pump 12 for delivering mortar towards the helical conveying rod 11 is provided at the bottom of the water collection tank 7.

The collection device comprises a collection chamber 13, on which a funnel 14 is provided for receiving the rock debris poured by the filtering scoop 10. A cleaning sprayer 15 is connected at the outlet of the funnel 14, and a fresh water pipe 16 is connected with the cleaning sprayer 15. The collection chamber 13 is provided therein with a rotating disk 17, to the bottom of which a stepper motor 18 is connected, and at the top of which a plurality of sand storing cylinders 19 are arranged in annular shape, and the cleaning sprayer 15 is arranged opposite to the inlets of the sand storing cylinders 19.

The catching and washing apparatus further comprises a controlling device, which comprises an explosion-proof box 20 having a controller, and the controller is connected to the driving device, the driving motor 8 and the stepper motor 18.

The function of the controlling device is to control electronic controlling elements in the entire catching and washing apparatus. The management is carried out in a centralized way, facilitating both the manipulation and the maintenance and repair in later stage, wherein the controlling device undergoes a sealing processing, because of working in watery environment. It is able to prevent water from entering the explosion-proof box 20 after undergoing the sealing processing, achieving safety and reliability.

At the inlet of the funnel 14 is a rain pipe provided, one end of which is closed, and the other end of which is placed in the water collection tank 7 and connected with a first water pump 21 connected to the controller.

The function of the rain pipe is to perform a first washing to the rock debris entering the funnel 14. The rock debris in the filtering scoop 10 after being filtered might be attached with small particles and other impurities. The rock debris may be rinsed well through the first washing, being advantageous to later-stage analysis.

Herein, during the first washing, the requirement on cleanliness of water is not high, and the water in the water collection tank 7 may be used. The water leaked out from the filtering scoop 10 flows into the water collection tank 7, and the internal impurities of the water deposit in the collection tank 7 to a certain degree. And during the first washing, cleaner water in the upper layer can be used, achieving an appropriate cleaning-effect.

A fresh water tank 22 is provided in the collection tank 7, and the fresh water tank 22 is provided with a fresh water inlet and a fresh water outlet, which is connected with the fresh water pipe 16, and at the fresh water outlet is a second pump 23 provided and connected to the controller.

The function of the fresh water tank 22 is to perform a second cleaning to the rock debris discharged from the funnel 14, and the rock debris is collected after being rinsed well. Since the rock debris being directly collected after this cleaning, fresh water is used for cleaning, and the fresh water in the fresh water tank is imported from the external.

A vehicle cleaning tank 24 is provided in the water collection tank 7, and the vehicle cleaning tank 24 is provided with a water inlet and a water outlet, which is communicated with the water collection tank 7 and connected to a third pump 25 connected to the controller.

The function of the vehicle cleaning tank 24 is to clean the inside of the water collection tank 7, when it needs to be cleaned, using the water in the vehicle cleaning tank 24. Cleaning water is introduced from the vehicle cleaning tank 24 to the water collection tank 7, thus completing the cleaning for the water collection tank 7.

A drainage port is provided on the water collection tank 7 and connected with a drainage pump 26, which is connected to the controller.

In order to facilitate cleaning the water collection tank 7, the drainage port is provided on the water collection tank 7 and the drainage pump 26 is provided at the drainage port. Sewage in the water collection tank 7 is discharged out of the water collection tank under action of the drainage pump 26.

A backup delivery pump 27 is provided at the bottom of the water collection tank 7.

The function of the backup delivery pump 27 is to ensure the continual and smooth discharging of the mortar deposited in the water collection tank 7. When the delivery pump 12 malfunctions or needs the closing-down and cooling-down, the backup delivery pump 27 may be started, so that the catching and washing machine continues to work, avoiding the disadvantage that the whole machine cannot run if the delivery pump 12 malfunctions.

The bottom of the water collection tank 7 is in a funnel shape and provided with an opening, and a solenoid valve 28 is provided on the opening.

The funnel shape of the bottom of the water collection tank 7 is beneficial to the collection of the deposited mortar, meanwhile, the solenoid valve 28 is provided at the middle of the bottom, such that during the discharging of the mortar, the mortar flows, due to its fluidity, to the solenoid valve 28, which more helps discharging the sewage.

Diameter of the screening cylinder 6 is gradually reduced from the middle of the screening cylinder towards the ends thereof.

The water entering the screening cylinder 6 is in vortex state under the action of the impeller 5 and applies a certain impact force on the side wall of screening cylinder. Since the filtering holes are provided in the side wall of the screening cylinder, part of the water may be filtered out at this time, achieving the effect of preliminary filtration.

A protective cover 29 for covering and connecting the screening cylinder 6, the filtering scoop 10 and the funnel 14 is provided on the top of the water collection tank 7, and the bottom of the protective cover 29 is connected to the water collection tank 7.

The function of the protective cover 29 is to prevent the acquisition device, the filtration device and the collection device from being directly exposed to the outside, and can avoid foreign objects from entering the catching and washing machine, so that the process of collecting samples cannot be effected and more accurate.

In the above, a middle-layer filter screen is provided at the middle of the sand storing cylinder 19, and a bottom-layer filter screen is provided at the bottom thereof. The size of meshes of the middle-layer filter screen is greater than that of meshes of the bottom-layer filter screen.

The meshes of the middle-layer filter screen are relatively larger, thus larger rock debris are collected correspondingly on this middle-layer filter screen, while the meshes of the bottom-layer filter screen are relatively smaller, thus smaller rock debris are collected correspondingly on this bottom-layer filter screen. This manner of layering acquisition facilitates a later-stage treatment and testing analysis.

When using the automatic rock debris catching and washing apparatus provided by the present invention, mixture of water and rock debris in the delivery pipe 1 enters the screening cylinder 6, in vortex state, under action of the impeller 5, and a first filtration is performed in the screening cylinder 6. After part of the water is filtered out, mixture of the rock debris and a small amount of water is discharged into the filtering scoop 10, in which a second filtration is performed, the water filtered out directly enters into the water collection tank 7. The rock debris after the filtration, in the filtering scoop 10, enters the funnel 14, under action of the pendulum bar, and then enters the sand storing cylinders 19 to be collected.

The operation is a full-automatic collection approach, which is performed fully automatically. During use, it is not necessary to real-time monitor the working condition of the catching and washing apparatus by manpower, and collecting regularly the rock debris collected into the sand storing cylinders 19 is enough. It is highly adaptable to the harsh environment due to the mechanized processing, with high accuracy and more accurate analysis on the geological conditions.

Finally, it should be noted that the above embodiments merely illustrate the technical solutions of the present invention, but are not intended to limit the present invention. Although the present invention has been described in detail referring to the foregoing embodiments, those skilled in the art will appreciate that the technical solutions described in the foregoing embodiments may be modified, or some or all of the technical features may be equivalently replaced, and such modifications or replacements do not enable the corresponding technical solutions to depart from the scope of the technical solutions of the various embodiments of the present invention.

The invention claimed is:

1. An automatic rock debris catching and washing apparatus, comprising an acquisition device, a filtration device and a collection device, the acquisition device comprising a delivery pipe, which has one end corresponding to an acquisition port and the other end as a delivery port, wherein the acquisition port is provided on an acquisition pipe, with the acquisition port in a strip shape, the delivery pipe is sleeved over the acquisition pipe, the acquisition pipe and the delivery pipe can make telescopic movement relative to each other, the delivery port is connected with a filtering head, which comprises a bearing provided on the delivery port, an impeller is provided in the bearing, the impeller is connected to a driving device, and one end of the bearing away from the delivery pipe is connected with a screening cylinder, which has one end fixedly connected with the bearing and is provided with filtering holes in a side wall of screening cylinder;

the filtration device comprising a water collection tank, above which a driving motor is provided, wherein the driving motor is connected with a pendulum bar, one end of which is connected with a filtering scoop for receiving rock debris flowing out of the screening cylinder, the water collection tank is provided therein with a helical conveying rod, which has one end located at a bottom of the water collection tank and the other end located outside of the water collection tank, and a delivery pump for delivering mortar towards the helical conveying rod is provided at the bottom of the water collection tank; and the collection device comprising a collection chamber, on which a funnel is provided for receiving rock debris poured by the filtering scoop, wherein a cleaning sprayer is connected at an outlet of the funnel, and a fresh water pipe is connected with the cleaning sprayer, the collection chamber is provided therein with a rotating disk, which has a bottom is connected to a stepper motor, and a top provided with a plurality of sand storing cylinders arranged in an annular shape, and the cleaning sprayer is arranged opposite to inlets of the sand storing cylinders.

2. The automatic rock debris catching and washing apparatus according to claim 1, further comprising a controlling device, which comprises an explosion-proof box having a controller, and the controller is connected to the driving device, the driving motor and the stepper motor.

3. The automatic rock debris catching and washing apparatus according to claim 2, wherein a rain pipe is provided at an inlet of the funnel, and the rain pipe has one end closed and the other end placed in the water collection tank and connected with a first water pump, which is connected to the controller.

4. The automatic rock debris catching and washing apparatus according to claim 2, wherein a fresh water tank is provided in the collection tank, the fresh water tank is provided with a fresh water inlet and a fresh water outlet, which is connected with the fresh water pipe, and at the fresh water outlet is a second pump provided and connected to the controller.

5. The automatic rock debris catching and washing apparatus according to claim 2, wherein a vehicle cleaning tank is provided in the water collection tank, the vehicle cleaning tank is provided with a water inlet and a water outlet, which is communicated with the water collection tank and connected to a third pump, which is connected to the controller.

6. The automatic rock debris catching and washing apparatus according to claim 2, wherein a drainage port is provided on the water collection tank and connected with a drainage pump, which is connected to the controller.

7. The automatic rock debris catching and washing apparatus according to claim 1, wherein a backup delivery pump is provided at a bottom of the water collection tank.

8. The automatic rock debris catching and washing apparatus according to claim 1, wherein a bottom of the water collection tank is in a funnel shape and provided with an opening, and a solenoid valve is provided on the opening.

9. The automatic rock debris catching and washing apparatus according to claim 1, wherein diameter of the screening cylinder is gradually reduced from middle of the screening cylinder towards ends of the screening cylinder.

10. The automatic rock debris catching and washing apparatus according to claim 1, wherein a protective cover for covering and connecting the screening cylinder, the filtering scoop and the funnel is provided on a top of the water collection tank, and a bottom of the protective cover is connected to the water collection tank.

\* \* \* \* \*